US011191726B2

(12) United States Patent
Weigt et al.

(10) Patent No.: US 11,191,726 B2
(45) Date of Patent: Dec. 7, 2021

(54) CARRIER PELLETS, METHOD FOR PRODUCTION THEREOF AND USE THEREOF

(71) Applicants: IPC PROCESS-CENTER GMBH & CO. KG, Dresden (DE); ADD Advanced Drug Delivery Technologies Ltd., Reinach (CH)

(72) Inventors: Antje Weigt, Dresden (DE); Wolfgang Kempe, Dresden (DE); Burkhard Schlütermann, Au (DE)

(73) Assignees: IPC PROCESS-CENTER GMBH & CO. KG, Dresden (DE); ADD Advanced Drug Delivery Technologies Ltd., Reinach (CH)

( * ) Notice: Subject to any disclaimer, the term of this patent is extended or adjusted under 35 U.S.C. 154(b) by 0 days.

(21) Appl. No.: 14/209,056

(22) Filed: Mar. 13, 2014

(65) Prior Publication Data

US 2014/0193509 A1    Jul. 10, 2014

Related U.S. Application Data

(63) Continuation of application No. 12/863,336, filed as application No. PCT/EP2009/000124 on Jan. 12, 2009.

(30) Foreign Application Priority Data

Jan. 17, 2008   (DE) .................. 10 2008 004 893.3

(51) Int. Cl.
  *A61K 9/16*     (2006.01)
  *A61K 47/12*    (2006.01)

(52) U.S. Cl.
  CPC .......... *A61K 9/1617* (2013.01); *A61K 9/1652* (2013.01); *A61K 9/1682* (2013.01); *A61K 9/1694* (2013.01); *A61K 47/12* (2013.01)

(58) Field of Classification Search
  None
  See application file for complete search history.

(56) References Cited

U.S. PATENT DOCUMENTS

| | | | |
|---|---|---|---|
| 5,463,100 A | 10/1995 | Walter | |
| 5,902,844 A | 5/1999 | Wilson | |
| 6,056,949 A | 5/2000 | Menzi et al. | |
| 6,492,024 B1 | 12/2002 | Walter | |
| 2001/0021404 A1* | 9/2001 | Uhlemann | A23G 3/346 426/89 |
| 2002/0123465 A1 | 9/2002 | Twardzik et al. | |
| 2002/0192290 A1* | 12/2002 | Seth | 424/488 |
| 2003/0158206 A1 | 8/2003 | Billotte et al. | |
| 2003/0211168 A1* | 11/2003 | Lynenskjold | A61K 9/1676 424/494 |
| 2003/0219489 A1 | 11/2003 | Curatolo et al. | |
| 2004/0228978 A1 | 11/2004 | Jacob et al. | |
| 2005/0163855 A1 | 7/2005 | Cho et al. | |
| 2006/0115539 A1 | 6/2006 | Prasch | |
| 2007/0281927 A1 | 12/2007 | Tyavanagimatt et al. | |
| 2008/0038347 A1* | 2/2008 | Eisenreich | A61K 9/2077 424/468 |
| 2008/0199592 A1 | 8/2008 | Fexer et al. | |

FOREIGN PATENT DOCUMENTS

| | | |
|---|---|---|
| DE | 197 33 094 | 2/1999 |
| DE | 198 82 382 | 5/2000 |
| EP | 1 262 198 | 12/2002 |
| EP | 1 317 925 | 6/2003 |
| EP | 1 818 047 | 8/2007 |
| EP | 1 958 520 | 8/2008 |
| JP | 03-047121 | 2/1991 |
| JP | 2007-297313 | 11/2007 |
| WO | WO 97/16078 | 5/1997 |
| WO | WO 98/53705 | 12/1998 |
| WO | WO 02/080678 | 10/2002 |
| WO | WO 2004/108266 | 12/2004 |
| WO | WO/2006/052503 | 5/2006 |
| WO | WO 2006/102964 | 10/2006 |

OTHER PUBLICATIONS

Chemical abstract: Database Accession No. 147:528145; 1 pg. (Dec. 2007).
Koraklaniti et al., *Journal of Drug Delivery Science and Technology*, vol. 14, No. 3, pp. 207-214 (2004).
Oneida et al., *Powder Technology*. vol. 130, pp. 377-394 (2003).
International Search Report for International Application No. PCT/EP2009/000124 dated Dec. 2, 2009.
English translation of the International Preliminary Report on Patentability for International Application No. PCT/EP2009/000124 dated Aug. 19, 2010.
Jacob et al., *Powder Technology*, vol. 189, No. 2, pp. 332-341 (2009).

* cited by examiner

*Primary Examiner* — Erin E Hirt
(74) *Attorney, Agent, or Firm* — Haug Partners LLP

(57) ABSTRACT

The invention relates to a method for the production of carrier pellets for pharmaceutical active substances. Likewise, the invention relates to such carrier pellets and also to pharmaceutical formulations containing these. The carrier pellets according to the invention are used for transporting and releasing pharmaceutical active substances, in particular in the human body.

30 Claims, No Drawings

CARRIER PELLETS, METHOD FOR PRODUCTION THEREOF AND USE THEREOF

The present application is a continuation of U.S. patent application Ser. No. 12/863,336 filed on Jul. 16, 2010, which claims priority from PCT Patent Application No. PCT/EP2009/000124 filed on Jan. 12, 2009, which claims priority from German Patent Application No. DE 10 2008 004 893.3 filed on Jan. 17, 2008, the disclosures of which are incorporated herein by reference in their entirety.

The invention relates to a method for the production of carrier pellets for pharmaceutical active substances. Likewise, the invention relates to such carrier pellets and also to pharmaceutical formulations containing these. The carrier pellets according to the invention are used for transporting and releasing pharmaceutical active substances, in particular in the human body.

Pharmaceutical administration forms which can be applied in particular orally are intended to be formulated suitably for the respective application in order to effect release of the pharmaceutical active substances at the correct time and without disturbing side-effects. Thus active substances which can be administered for example orally are intended to be released as far as possible such that an unpleasant, e.g. bitter, taste in the mouth is avoided since this can lead to reactions of repulsion in particular in children. On the other hand, the active substances must be released in the stomach or intestine as completely as possible and in a rapidly absorbable form if a systemic treatment is sought.

In the case of oral administration of drugs, the active substance is released in the gastro-intestinal tract and a part of the active substance is absorbed. By controlling the release of the active substance, the degree of absorption and the effective duration can be influenced. Correspondingly, various proposals have been made for controlling release of the active substance by suitable galenic formulations of the active substance.

One approach resides in providing administration forms with coatings, release of the active substance being able to be influenced as a function of the solubility or permeability of the coatings. Such coatings can be applied for example on tablets or capsules. In this case, a disadvantage exists however in that a faulty or damaged coating can lead to the fact that the release of the total active substance dose is not controlled in the desired manner.

There are possible, as an alternative, multiparticulate administration forms in which the total quantity of the active substance is apportioned to a larger number of smaller units, such as pellets. If the individual pellets are provided with coatings, then, in the case of a faulty coating in one pellet, only a correspondingly small proportion of the total active substance dose is not subjected to the desired release.

A further advantage of such administration forms based on pellets resides in the fact that sufficiently small pellets pass into the intestine from the stomach relatively rapidly after ingestion. On the other hand, tablets, as long as they do not disintegrate, can also remain in the stomach for a fairly long time, the time in addition being very variable.

Known administration forms with controlled release are hence not entirely satisfactory. In addition, the problem exists that desired (prescribed) release profiles generally cannot be set. Furthermore, the production of administration forms with controlled release is often difficult. Hence there is a requirement for new administration forms with controlled release and also for new methods for the production of administration forms with controlled release.

It was therefore the object of the present invention to provide carrier pellets and a method for the production thereof, which enable a controlled release of the loaded, pharmaceutically effective component and which do not have the disadvantages of the systems known from the state of the art.

This object is preferably achieved by the characterizing features of the invention. Advantageous embodiments and further developments will be apparent from the description of the invention provided herein.

According to the invention, a method for the production of carrier pellets for an active substance is provided in which
a) a liquid formulation is produced by dissolving and/or dispersing at least one physiologically well-tolerated pH regulator in at least one solvent or emulsifier,
b) the liquid formulation is introduced by means of nozzles into a fluidised bed- or spouted bed unit,
c) essentially spherical carrier pellets are formed by spray granulation in the unit in which the solvent is evaporated by means of a drying gas flow and
d) the carrier pellets are discharged continuously from the unit.

It is preferred that a pH regulator which has a regulating effect in the physiological surroundings is used, such that the pH value is lowered or increased and hence the bioavailability of pharmaceutically effective components is made possible or increased. This can however also be achieved in that the pH regulator has a stabilising function, e.g. when using a buffer system as pH regulator.

Preferably, the pH regulator is an organic acid, this being selected particularly preferably from the group comprising $C_1$-$C_{18}$ mono-, di- and tricarboxylic acids and also mixtures thereof. Representatives of this group, given by way of example, are citric acid, succinic acid, malic acid, fumaric acid, tartaric acid, sorbic acid, adipinic acid, salts and mixtures thereof. It is likewise possible that ascorbic acid or salts thereof are used as pH regulator.

A further preferred embodiment provides that the at least one pH regulator is an acidic or basic salt.

If the pH regulator is a buffer system, then this preferably comprises an acidic or basic salt together with a corresponding caustic solution or acid. Examples of these are citric acid/citrate or tartaric acid/tartrate.

In a further preferred variant, the pH regulator is an organic base, e.g. a purine base or a pyrimidine base, or a mixture of these bases. The purine base is preferably selected from the group comprising adenine, guanine, hypoxanthine, xanthine and mixtures hereof. The pyrimidine base is preferably selected from the group comprising cytosine, uracil, thymine and mixtures hereof.

In the case where the pH regulator is a basic inorganic salt, this is preferably selected from the group comprising $NaHCO_3$, $K_2CO_3$, $Na_2CO_3$, $KHCO_3$, $Ca(OH)_2$, $CaO$, phosphates and mixtures hereof.

Preferably, the formulation contains in addition at least one physiologically well-tolerated binder. This binder is thereby preferably selected from the group comprising methyl celluloses, hydroxymethyl celluloses, hydroxypropylmethyl celluloses, alginates, pectins, polyvinylpyrrolidones, xanthanes and also other hydrocolloids and mixtures hereof.

Preferably water or organic solvents are used as solvents or emulsifiers. As organic solvents, particularly preferred are ethyl alcohol, isopropanol, n-propanol or mixtures thereof.

The quantity ratio of pH regulator to binder in the liquid formulation is preferably in the range of 50:50 to 99:1. A preferred liquid formulation has 30 to 80% by weight of the at least one pH regulator, 0.5 to 5% by weight of the at least one binder and 15 to 69.5% by weight of the at least one solvent.

The spray granulation can be effected both in a fluidised bed unit and in a spouted bed unit. The temperature in these units is thereby preferably in the range of 5 to 100° C. The drying gas flow entering the coating unit has, at the entrance into the unit, preferably a temperature in the range of 5 to 120°. There are possible as drying gas, its particular conditioned air, nitrogen or inert gases, e.g. noble gases.

If the spray granulation is effected in a fluidised bed unit, the drying gas is supplied via a sieve plate. At the same time, the liquid formulation is introduced into the unit by nozzles disposed above the sieve plate.

If the spray granulation is effected in a spouted bed unit, then the drying gas is supplied through longitudinal gaps situated on the bottom. The liquid formulation is introduced via at least one nozzle disposed between the longitudinal gaps.

Preferably, introduction of the liquid formulation is effected through the nozzle from below to above.

According to the invention, likewise carrier pellets which contain at least one physiologically well-tolerated pH regulator are provided. These carrier pellets are produced according to the above-described method.

The carrier pellets preferably have a diameter in the range of 50 μm to 1.5 mm, in particular of 90 μm to 1.2 mm.

The carrier pellets are thereby preferably essentially spherical. The carrier pellets preferably have a sphericity of 0.8 to 1.0, in particular of 0.9 to 1.0.

The sphericity is thereby calculated according to the following formula:

$$SPHT = \frac{4\pi A}{U^2}$$

with A=surface area and U=circumference.

The sphericity can be implemented with devices for particle size- and particle shape analysis with dynamic image analysis. A device suitable for this purpose is for example the CAMSIZER by Retsch Technology.

Furthermore, it is preferred that the ratio of width to length of the carrier pellets is in the range of 0.8 to 1.0, in particular of 0.9 to 1.0. The ratio of width to length is thereby calculated according to the following formula:

$$b/l = \frac{\min(x_c)}{\max(x_{Fe})}$$

with $x_{Fc}$=Feret diameter and $x_c$=maximum width of the particle.

Also the width-length ratio can be determined for example with the mentioned CAMSIZER.

Preferably, the carrier pellets according to the invention concern dense carrier pellets, which implies a weight reduction relative to extrusion pellets.

The carrier pellets have essentially the same particle size, i.e., a narrow scatter range with respect to the particle size is present.

The carrier pellets preferably contain at least one physiologically well-tolerated binder. This binder is thereby preferably selected from the group comprising methyl celluloses, hydroxymethyl celluloses, hydroxypropylmethyl celluloses, alginates, pectins, polyvinylpyrrolidones, xanthanes and also other hydrocolloids and also mixtures hereof.

According to the invention, likewise a pharmaceutical formulation is provided, containing the above-described carrier pellets and at least one active substance.

The carrier pellets according to the invention are used as carrier structure for pharmaceutically effective components.

EXAMPLE

Production of Dicarboxylic Acid Pellets by Means of D/L Malic Acid
1.1 Production of the Spray Solution The spray solution comprises purified water, methyl cellulose and malic acid. A 4% binder solution is produced from the purified water and methyl cellulose. This is temperature-controlled at 70° C. Thereafter, the addition of malic acid is effected with constant agitation until a complete solution is present (proportion of purified water corresponds to proportion of malic acid).

1.2 Particle Formation

The temperature-controlled spray solution is sprayed into the spouted bed apparatus (ProCell) in the bottom spray method. A constant particle formation is effected by atomising the solids solution in the main airflow. The latter comprises two partial flows which are produced through gap openings, leading along through the process chamber. The particle construction takes place by evaporation of the solvent water, malic acid and methyl cellulose remain in the airflow dried as particles. By means of the defined flow profile of the apparatus, the particles in the upper process chamber separate from the central airflow and flow laterally, caused by gravity and the suction effect of the main airflow, back towards the process gas inlet. There, they are entrained again with the main airflow and coated continuously with solids from the spray solution. The process air is conditioned.

During the continuous introduction of the solids mixture via atomisation, the removal of acidic pellets is effected at the same time. The malic acid pellets are fractionated for the desired particle size.

Undersize particles and prepared oversize particles can thereby be returned to the process. The end product is a homogeneous virtually spherical malic acid pellet with a uniform surface structure.

The invention claimed is:

1. A method for the production of carrier pellets for a pharmaceutically active substance, the method comprising:
    a) producing a liquid formulation by dissolving, dispersing, or a combination of dissolving and dispersing at least one pH regulator in at least one solvent, wherein the liquid formulation contains:
        30 to 80% by weight of the at least one pH regulator; and
        15 to 69.5% by weight of the at least one solvent;
    b) introducing the liquid formulation into a fluidized bed or spouted bed unit using at least one nozzle;
    c) forming essentially spherical carrier pellets by spray granulation in the unit wherein the solvent is evaporated by a drying gas flow; and
    d) discharging the carrier pellets from the unit;
    wherein, in step b), the fluidized bed or spouted bed unit is empty so that the carrier pellets are formed in step c) from only the liquid formulation.

2. The method according to claim 1;
wherein the at least one pH regulator has a regulating effect in physiological surroundings such that the pH value is lowered or increased and the bioavailability of the pharmaceutically active substance is made possible or increased.

3. The method according to claim 1;
wherein the at least one pH regulator comprises at least one organic acid selected from the group consisting of ascorbic acid, a $C_1$-$C_{18}$ monocarboxylic acid, a $C_1$-$C_{18}$ dicarboxylic acid, a $C_1$-$C_{18}$ tricarboxylic acid and mixtures thereof.

4. The method according to claim 3;
wherein the at least one organic acid is selected from the group consisting of citric acid, succinic acid, malic acid, fumaric acid, tartaric acid, sorbic acid, adipinic acid, salts thereof, and mixtures thereof.

5. The method according to claim 1;
wherein the at least one pH regulator comprises an acidic or basic salt.

6. The method according to claim 1;
wherein the pH regulator comprises a buffer system comprising an organic acid and salt of the organic acid or an organic base and salt of the organic base, wherein the buffer system stabilizes the pH.

7. The method according to claim 6;
wherein the buffer system comprises at least one combination selected from the group consisting of:
citric acid and a citrate; and
tartaric acid and a tartrate.

8. The method according to claim 1;
wherein the pH regulator acts in physiological surroundings as pH-increasing, pH lowering, or pH-stabilising.

9. The method according to claim 1;
wherein the pH regulator comprises at least one organic base selected from the group consisting of a purine base, a pyrimidine base, and a mixture thereof.

10. The method according to claim 9;
wherein the purine base is selected from the group consisting of adenine, guanine, hypoxanthine, xanthine, and mixtures thereof.

11. The method according to claim 9;
wherein the pyrimidine base is selected from the group consisting of cytosine, uracil, thymine, and mixtures thereof.

12. The method according to claim 1;
wherein the pH regulator comprises at least one basic inorganic salt selected from the group consisting of $NaHCO_3$, $K_2CO_3$, $Na_2CO_3$, $KHCO_3$, $Ca(OH)_2$, $CaO$, phosphates, and mixtures thereof.

13. The method according to claim 1;
wherein the liquid formulation further comprises at least one binder.

14. The method according to claim 13;
wherein the at least one binder is selected from the group consisting of methyl celluloses, hydroxymethyl celluloses, hydroxypropylmethyl celluloses, alginates, pectins, polyvinylpyrrolidones, xanthanes, hydrocolloids, and mixtures thereof.

15. The method according to claim 1;
wherein the at least one solvent is water or an organic solvent selected from the group consisting of ethyl alcohol, isopropanol, n-propanol, and mixtures thereof.

16. The method according to claim 13;
wherein the quantity ratio of pH regulator to binder in the liquid formulation is in the range of 50:50 to 99:1.

17. The method according to claim 1;
wherein the temperature in the unit is in the range of 5 to 100° C.

18. The method according to claim 1;
wherein the drying gas flow has, at the entrance into the unit, a temperature in the range of 5 to 120°.

19. The method according to claim 1;
wherein the drying gas is air, nitrogen, or inert gas.

20. The method according to claim 1;
wherein the spray granulation is effected in a fluidized bed unit into which the drying gas is supplied via a sieve plate and the liquid formulation is introduced by the at least one nozzle disposed above the sieve plate.

21. The method according to claim 1;
wherein the spray granulation is effected in a spouted bed unit into which the drying gas is supplied via longitudinal gaps disposed in the lower half of the unit and the liquid formulation is introduced by the at least one nozzle disposed between the longitudinal gaps.

22. The method according to claim 21;
wherein the introduction of the liquid formulation is effected through the nozzle from below to above.

23. The method according to claim 1;
wherein the essentially spherical carrier pellets formed to have a sphericity of 0.8 to 1.0.

24. The method according to claim 1;
wherein the essentially spherical carrier pellets formed to have a sphericity of 0.9 to 1.0.

25. The method according to claim 13;
wherein the at least one binder is present in the liquid formulation in an amount of 0.5 to 5% by weight.

26. The method according to claim 1;
wherein no pharmaceutically active substance is fed into the fluidized bed or spouted bed unit so that the carrier pellets discharged from the unit contain no pharmaceutically active substance.

27. The method according to claim 1;
wherein the liquid formulation contains 41 to 80% by weight of the at least one pH regulator.

28. The method according to claim 27;
wherein the liquid formulation contains 45 to 80% by weight of the at least one pH regulator.

29. The method according to claim 1;
wherein the liquid formulation contains 50 to 80% by weight of the at least one pH regulator.

30. The method according to claim 1;
wherein the liquid formulation further comprises at least one binder; and
wherein the liquid formulation has a ratio of total pH regulator to total binder of 50:50 to 99:1 so that the carrier pellets have a have a total pH regulator amount of 50 to 99% after the solvent is evaporated by the drying gas flow.

* * * * *